(12) United States Patent
Hesselink et al.

(10) Patent No.: US 11,391,679 B2
(45) Date of Patent: Jul. 19, 2022

(54) HOLOGRAPHIC X-RAY DETECTION

(71) Applicant: The Board of Trustees of the Leland Stanford Junior University, Stanford, CA (US)

(72) Inventors: Lambertus Hesselink, Atherton, CA (US); George Kiyoshi Herring, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/169,061

(22) Filed: Feb. 5, 2021

(65) Prior Publication Data
US 2021/0247330 A1  Aug. 12, 2021

Related U.S. Application Data

(60) Provisional application No. 62/971,677, filed on Feb. 7, 2020.

(51) Int. Cl.
*G01N 23/041* (2018.01)
*G21K 1/06* (2006.01)
*G01N 23/083* (2018.01)

(52) U.S. Cl.
CPC ......... *G01N 23/041* (2018.02); *G01N 23/083* (2013.01); *G21K 1/065* (2013.01); *G21K 2207/005* (2013.01)

(58) Field of Classification Search
CPC .... G01N 23/041; G01N 23/083; G21K 1/065; G21K 2207/005
See application file for complete search history.

(56) References Cited

U.S. PATENT DOCUMENTS

| | | | |
|---|---|---|---|
| 8,879,137 B2 | 11/2014 | Stewart et al. | |
| 2003/0073007 A1* | 4/2003 | Lahrichi | G11C 13/0033 430/1 |
| 2013/0108020 A1 | 5/2013 | Mukaide | |

OTHER PUBLICATIONS

Berben et al. "Photorefractive x-ray imaging" University of Bonn, Institute of Physics, Germany, Applied Physics Letters, vol. 81, No. 9, Aug. 2002, p. 1567-1569 (Year: 2002).*
Goodman, Joseph W., "Introduction to Fourier optics" Roberts and Company Publishers, 2005. pp. 312-314.

* cited by examiner

*Primary Examiner* — David P Porta
*Assistant Examiner* — Mamadou Faye
(74) *Attorney, Agent, or Firm* — Beyer Law Group LLP

(57) ABSTRACT

An apparatus for X-ray imaging is provided. An X-ray source provides an X-ray along an X-ray beam path. A holographic medium is along the X-ray beam path. An X-ray phase grating is between the X-ray source and the holographic medium along the X-ray beam path. A readout beam source provides a readout beam along a readout beam path. A readout detector is along the readout beam path, wherein the holographic medium is along the readout beam path.

11 Claims, 5 Drawing Sheets

HOLOGRAPHIC X-RAY DETECTION

CROSS-REFERENCE TO RELATED APPLICATION

This application claims the benefit of priority of U.S. Application No. 62/971,677, filed Feb. 7, 2020, which is incorporated herein by reference for all purposes.

BACKGROUND

This disclosure relates generally to X-ray imaging. More specifically, the disclosure relates to differential phase contrast (DPC) X-ray imaging. Traditional X-ray imaging is only capable of measuring the absorptivity of an object. Such imaging detects bones but leaves much to be desired when differentiating soft tissues or telling the difference between powders and liquids. DPC X-ray imaging adds the ability to measure the differential phase and small angle scattering properties of materials in addition to absorption. The addition of phase and scatter images provides information about the refractive index and sub-resolution features. DPC scatter imaging has several useful capabilities such as distinguishing between powders and liquids, between healthy lung tissue and damaged, and between homogeneous and heterogeneous materials. Collection of this information is possible because X-rays are absorbed, refracted, and scattered when they pass through an object. Measuring the extent to which an object absorbs, refracts, or scatters light is made possible by spatially patterning the X-ray beam by adding a G1 phase grating. The phase grating causes portions of the X-ray beam to interfere and results in a modulation in X-ray intensity or X-ray fringes. The modulation caused by the G1 phase grating is the result of the interference between the diffractive orders from the G1 grating. The interference of the diffractive orders encodes both the phase shift and absorption of the X-ray beam by the object under inspection.

SUMMARY

In accordance with the invention, an apparatus for X-ray imaging is provided. An X-ray source provides an X-ray along an X-ray beam path. A holographic medium is along the X-ray beam path. An X-ray phase grating is between the X-ray source and the holographic medium along the X-ray beam path. A readout beam source provides a readout beam along a readout beam path. A readout detector is along the readout beam path, wherein the holographic medium is along the readout beam path.

In another manifestation, a method, for detecting a spatially varying X-ray intensity pattern is provided. X-rays are directed into a photorefractive medium. A spatially varying index of refraction modulation induced by the X-ray intensity pattern in the photorefractive medium is read out.

The invention and objects and features thereof will be more readily apparent from the following detailed description and appended claims when taken with the drawings.

BRIEF DESCRIPTION OF THE DRAWINGS

The present disclosure is illustrated by way of example, and not by way of limitation, in the figures of the accompanying drawings and in which like reference numerals refer to similar elements and in which.

DETAILED DESCRIPTION OF ILLUSTRATED EMBODIMENTS

Figure 1:
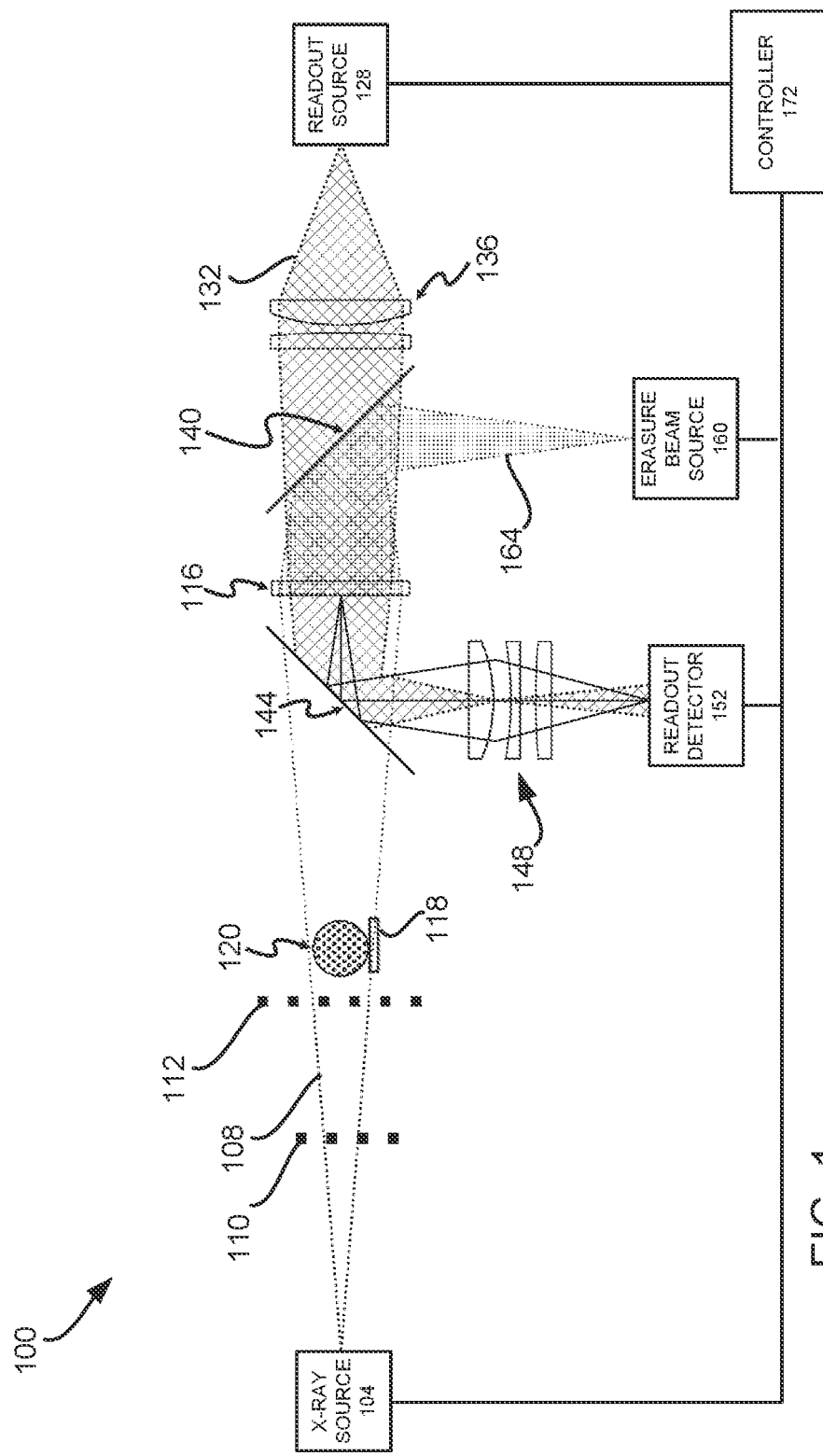
FIG. 1 is a schematic view of a holographic X-ray differential phase contrast detection system of an embodiment.

X-ray Differential Phase Contrast (DPC) imaging is the next generation of X-ray imaging in medical applications and non-destructive testing. Traditional X-ray imaging is only capable of measuring the absorptivity of an object. This process makes bones easy to detect but leaves much to be desired when differentiating soft tissues or telling the difference between powders and liquids. X-ray DPC adds in the ability to measure, in addition to absorption, the differential phase and small angle scattering properties of materials. The addition of phase and scatter images provides information about the refractive index and sub-resolution features. DPC scatter imaging has several useful capabilities such as distinguishing between powders and liquids, between healthy lung tissue and damaged, and between homogeneous and heterogeneous materials. The differential phase measurement from DPC provides an additional metric, in conjunction with absorption, for material identification and highlights changes across the image in thickness, density, or material type. Collection of this information is possible because X-rays are absorbed, refracted, and scattered when they pass through an object, just as any other type of electromagnetic wave. Measuring the extent to which an object absorbs, refracts, or scatters light is made possible by spatially patterning the X-ray beam by adding a G1 phase grating. The phase grating causes portions of the X-ray beam to interfere and results in a modulation in X-ray intensity or X-ray fringes. The modulation caused by the G1 phase grating is the result of the interference between the diffractive orders from the G1 grating. The interference of the diffractive orders encodes both the phase shift and absorption of the X-ray beam by the object under inspection. Thus the X-ray fringes are a hologram of the object being imaged.

The X-ray fringes are distorted due to the refraction of X-rays by the object being imaged. The extent of the distortion can be measured and results in a differential phase contrast image. The object also simultaneously absorbs some of the X-rays which results in an absorption image. Finally, the object causes some of the X-rays to scatter at small angles with scattering maximized at interfaces. In the example of a uniform sphere, this results in a scatter signal at the edges of the sphere. If the material was fibrous, sponge-like, or made of powder then those internal interfaces would result in a scatter signal from the bulk of the object as well.

The state of the art in X-ray DPC measurement is somewhat more complicated due to the lack of ultra high resolution X-ray detectors. When X-rays passing through a reasonably small object on the order of 1 cm are only refracted by a small angle, on the order of $10^{-6}$ radians. This results in the X-ray fringes being distorted on the order of $10^{-1}$ μm. In order to measure such a tiny distortion accurately, the X-ray fringes themselves must be within a couple of orders of magnitude in size to accurately measure the induced distortion, on the order of 1 μm to 10 μm. However, commercially available X-ray detectors are not capable of resolving features smaller than roughly 30 μm at 40 keV without significant (>90%) loss in quantum efficiency. This problem can be partially resolved by adding a G2 absorption grating into the beam line directly in front of the X-ray detector. The G2 absorption grating, in conjunction with the X-ray fringes, forms a Moire pattern on the X-ray detector at a low resolution. Where the X-ray fringes are in phase with the G2 grating, the fringes can pass through the slits and a high intensity is detected by the X-ray detector. Where the X-ray fringes are out of phase with the G2 grating, the X-ray grating absorbs a large fraction of the incident X-rays and the X-ray detector detects low intensity. The use of a G2 grating also, unfortunately, comes with several drawbacks. The G2 grating has a 50% duty cycle, so it results in a 50% signal loss on average. In a medical context, this means the patient is being exposed to twice the radiation dose as is actually being measured by the X-ray detector. The G2 grating must also be precisely aligned and any misalignment or manufacturing irregularity results in image artifacts. Typically, the G2 grating must also be moved back and forth to separate measurements in phase from measurements in absorption as both are presented to the detector as shifts in intensity. These drawbacks of using a G2 grating hinder the adoption of X-ray DPC overall as an imaging technique.

X-ray DPC is of critical importance during and after the COVID-19 pandemic due to its ability to more clearly differentiate between healthy and damaged lung tissue. There is substantial evidence that even those who survive COVID-19, but require ventilation, are left with significant lung damage. X-ray DPC will be a critical tool in the early detection of the next respiratory disease, as SARS-CoV-2 is only the latest new virus in a century that has already seen SARS, MERS, and H1N1. However, despite a general acknowledgment of the benefits provided by X-ray DPC imaging, it has not been commonly adopted as a commercial instrument. The roadblock for DPC imaging lies not with the technique itself, but rather the lack of high resolution, high energy, and high quantum efficiency X-ray detectors.

The primary limitation in X-ray DPC imaging is not X-ray DPC imaging as a technique, but rather in the lack of sufficiently high resolution X-ray detectors which are also capable of operating at high energies and with high quantum efficiency. There are many methods of X-ray detection but spatially resolved digital X-ray detection is generally divided into direct and indirect X-ray detection. Direct X-ray detection uses a semiconductor material with an applied bias field. When an X-ray interacts with the material a charge cloud is produced which separates in the bias field and drifts to the anode and cathode of the detector. Direct X-ray detectors cannot come close to the desired resolution both due to defects in the semiconductor material and that the material must be roughly two orders of magnitude thicker than the desired resolution in order to maintain high quantum efficiency. The charge clouds diffuse and scatter too much over this thickness to achieve the desired resolution. High resolution X-ray detectors which are commercially available typically use indirect X-ray detection. Indirect X-ray detection uses a scintillator that converts a portion of incident X-ray energy into visible light which can be collected and imaged onto a digitizer such as a photodiode array, CMOS detector, or CCD camera. The high efficiency design must use a thick scintillator to have sufficient stopping power to absorb the majority of incident X-rays. However, this results in most of the scintillator being out of focus for the high NA (numerical aperture) optics, resulting in a blurring on the digitizer. The detector must use high NA optics because only a portion of the incident X-ray energy is converted into visible light. Any light which isn't collected results in a decrease in signal to noise ratio (SNR) of the detector. The resolution can be improved by using a thinner scintillator. However, then, the majority of X-rays pass through the scintillator without interacting and are never detected. This is a strict tradeoff. Choosing a different scintillation material results in a slightly different trade-off but does not provide the desired improvement. There are efforts to develop better scintillation materials. Micro-columnar structures attempt to bypass the efficiency to resolution trade-off but have met with only limited success. Extended depth of field techniques are not applicable in this case due to the statistical and incoherent properties of the X-ray beam and its interaction with the scintillator. In order for an X-ray detector to be useful for X-ray DPC imaging, it would need to achieve >200 lp/mm and >80% quantum efficiency at 40 keV. Indirect X-ray detectors using LuAG:Ce operating at 200 lp/mm would have only 2% quantum efficiency at 40 keV.

An embodiment using Holographic X-ray detection is capable of both high resolution at 208 lp/mm and high quantum efficiency X-ray detection at 80% even for high energy X-rays in the 40 keV range. Holographic X-ray detection used in an embodiment operates in three stages; an X-ray hologram is written into a photorefractive crystal, the recorded hologram is read using visible light, and finally, the hologram is erased using uniform UV illumination. The separation of holographic X-ray detection into these three stages avoids the limitations of indirect X-ray detection since the number of visible photons detected by the digitizer is not limited by the energy of incident X-rays.

To facilitate understanding, FIG. 1 is a schematic view of a holographic X-ray differential phase contrast (DPC) detection system 100. The holographic X-ray differential phase contrast detection system 100 comprises an X-ray source 104 for providing an X-ray beam 108. A source amplitude grating 110, an X-ray phase grating 112, and a holographic medium 116 are placed along the path of the X-ray beam 108. An object support 118 supports an object 120 to be imaged between the X-ray phase grating 112 and the holographic medium 116 along the X-ray beam 108 path.

A readout beam source 128 provides a readout beam 132. Readout forming optics 136, such as lenses or mirrors are along the path of the readout beam 132. A beam combiner 140, the holographic medium 116, an optical mirror 144, an imaging system 148, and a readout detector 152 are along the readout beam 132 path.

An erasure beam source 160 provides an erasure beam 164 along an erasure beam path. The beam combiner 140 directs the erasure beam 164 to the holographic medium 116.

A controller 172 is configured to be electrically connected to the X-ray source 104, the readout detector 152, the erasure beam source 160, and the readout beam source 128. In other embodiments, more or fewer components may be configured to be electrically connected to the controller 172. For example, the readout forming optics 136 and the imaging system 148 may also be configured to be electrically connected to and controlled by the controller 172. The controller 172 may be a single computer system or separate computer systems. The separate computer systems may be stand-alone or may be networked together with each other or with other computer systems. The controller 172 may be used to control various components, such as the X-ray source 104, the readout detector 152, the erasure beam source 160, the readout forming optics 136, the imaging system 148, and the readout beam source 128. The controller 172 may receive and process data from various components such as the X-ray source 104, the readout detector 152, the erasure beam source 160, the readout forming optics 136, the imaging system 148, and the readout beam source 128.

Figure 2:
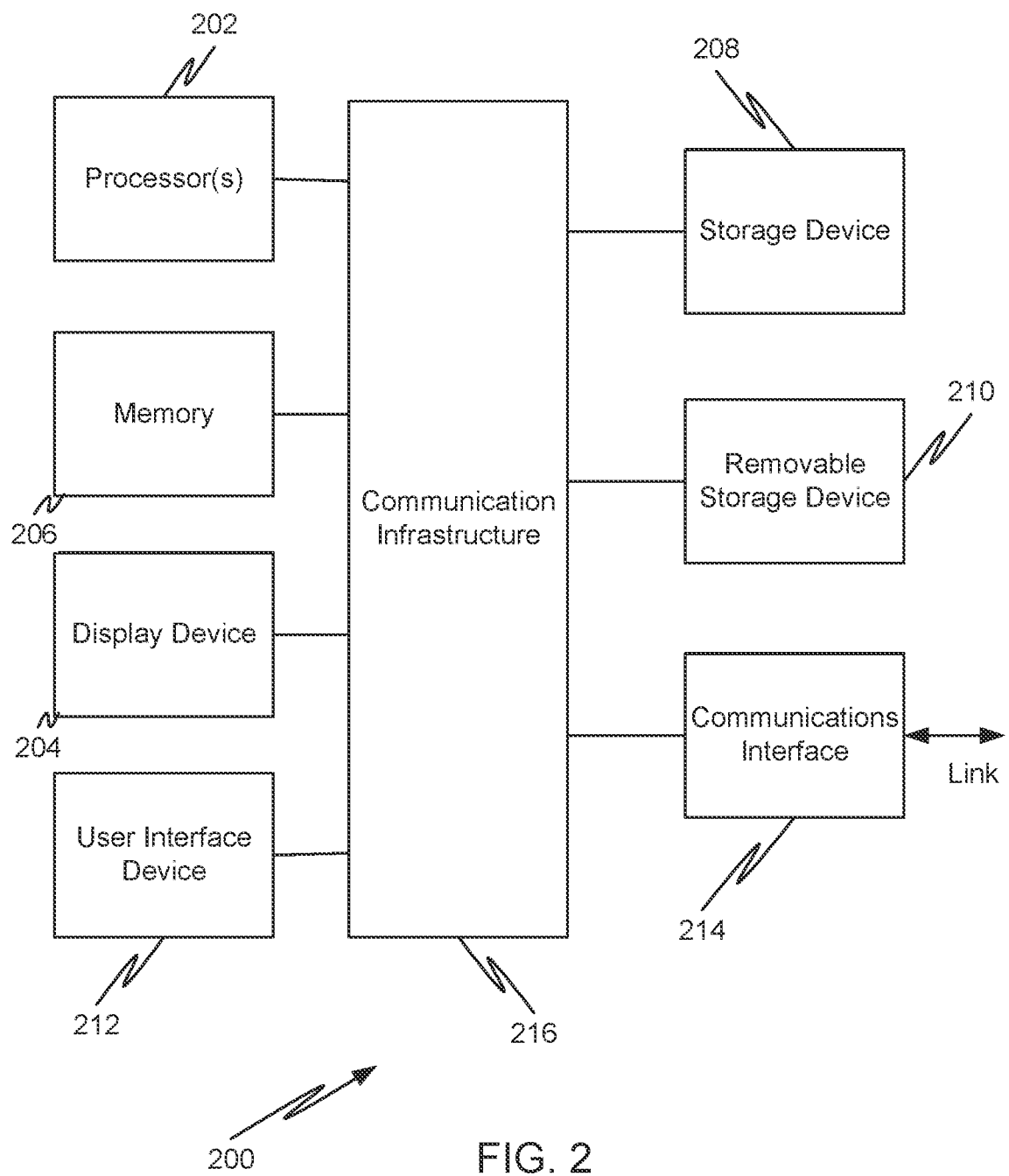
FIG. 2 is a high-level block diagram showing a computer system, which may be used to provide a controller.

FIG. 2 is a high-level block diagram showing a computer system 200, which may be used to provide the controller 172. The computer system may have many physical forms ranging from an integrated circuit, a printed circuit board, and a small handheld device up to a computer. The computer system 200 includes one or more processors 202, and further can include an electronic display device 204, a main memory 206 (e.g., random access memory (RAM)), data storage device 208 (e.g., hard disk drive), removable storage device 210 (e.g., optical disk drive), user interface devices 212 (e.g., keyboards, touch screens, keypads, mice or other pointing devices, etc.), and a communication interface 214 (e.g., wireless network interface). The communication interface 214 allows software and data to be transferred between the computer system 200 and external devices via a link. The system may also include a communications infrastructure 216 (e.g., a communications bus, cross-over bar, or network) to which the aforementioned devices/modules are connected.

Information transferred via communications interface 214 may be in the form of signals such as electronic, electromagnetic, optical, or other signals capable of being received by communications interface 214, via a communication link that carries signals and may be implemented using wire, cable, fiber optics, a phone line, a cellular phone link, a radio frequency link, and/or other communication channels. With such a communications interface, it is contemplated that the one or more processors 202 might receive information from a network, or might output information to the network in the course of performing the above-described method steps. Furthermore, method embodiments of the present invention may execute solely upon the processors or may execute over a network such as the Internet in conjunction with remote processors that share a portion of the processing.

The term "non-transient computer readable media" is used generally to refer to media such as main memory, secondary memory, removable storage, and storage devices, such as hard disks, flash memory, disk drive memory, CD-ROM, and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Figure 3:
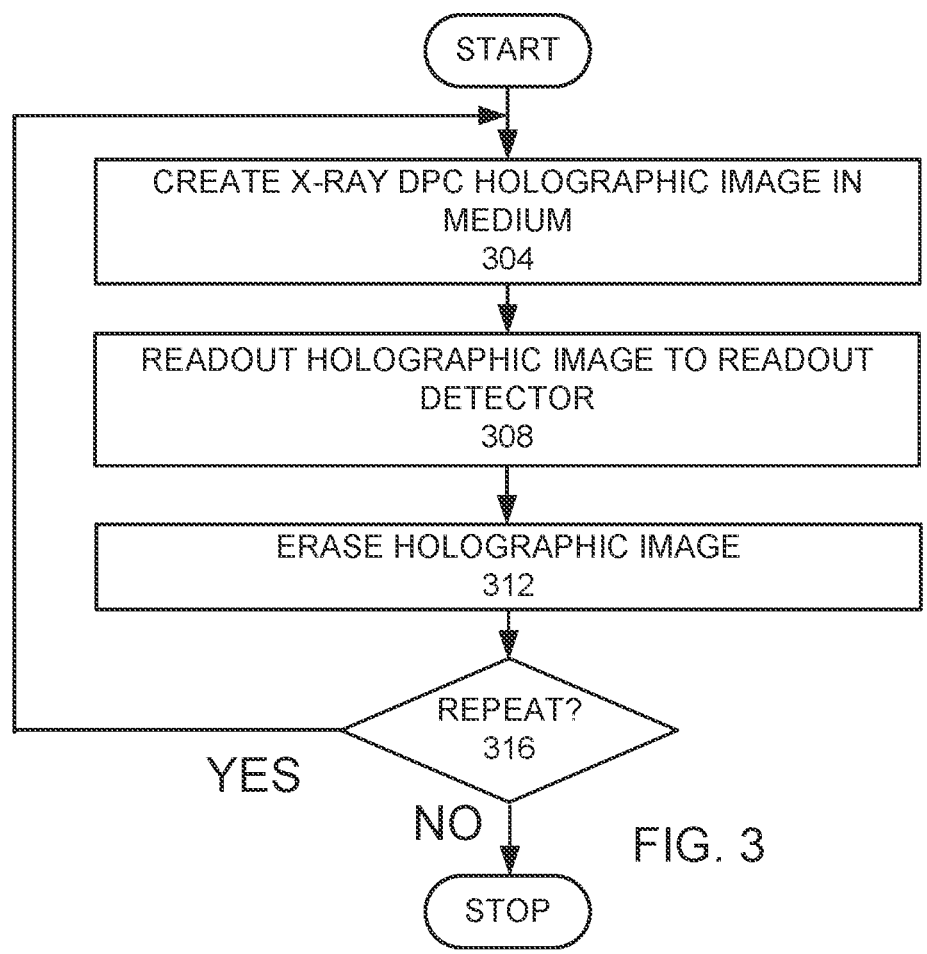
FIG. 3 is a high level flow chart of an embodiment.

FIG. 3 is a high level flow chart of an embodiment. An X-ray DPC holographic image is created in the holographic medium 116 (step 304). The X-ray source 104 provides the X-ray beam 108 through the source amplitude grating 110 and the X-ray phase grating 112, which passes through the object 120 and then to the holographic medium 116. The X-ray beam 108, X-ray phase grating 112, and the object create a holographic DPC X-ray image in the holographic medium 116. When this step is completed, the irradiation of the holographic medium 116 by the X-ray beam 108 is stopped.

After the X-ray DPC holographic image is created, the X-ray DPC holographic image is read out (step 308). A readout beam 132 from the readout beam source 128 passes through the holographic medium 116 to the readout detector 152. Readout forming optics 136 and an imaging system 148 are used to focus and direct the readout beam 132 to allow the reading out of the X-ray DPC holographic image. In this embodiment, the optical mirror 144 is used to bend the readout beam 132 to the readout detector 152, while allowing the X-ray beam 108 to pass to the holographic medium 116. The readout detector 152 records the readout beam 132 and sends recorded readout data to the controller 172, where the controller 172 creates a DPC X-ray image of the object. After the X-ray DPC holographic image readout is completed, the irradiation of the holographic medium 116 by the readout beam 132 may be stopped.

After the X-ray DPC holographic image readout is completed, the X-ray DPC holographic image may be erased (step 312). The erasure beam source 160 irradiates the holographic medium 116 with the erasure beam 164. The beam combiner 140 in this embodiment allows both the erasure beam 164 and the readout beam 132 to be directed to the holographic medium 116. By erasing the X-ray DPC holographic image in the holographic medium 116, the holographic medium 116 is available to provide another image for the same object or provide an image of another object (step 316). In some embodiments, an image of the same object may be made at a different position or angle.

In some embodiments, one or more of the steps may be controlled by the controller 172. The controller 172 may comprise computer readable code for performing one or more or all of the steps. The controller may further comprise computer readable code for generating and displaying an X-ray DPC image generated from the data from the readout detector 152. The controller 172 may further contain computer readable code for moving at least one of the object 120, X-ray beam 108, and holographic medium 116 with respect to each other.

In an embodiment, the X-ray phase grating 112 is an absorption grating to avoid interaction effects between the X-ray phase grating 112 performance in the holographic X-ray differential phase contrast detection system 100 and holographic X-ray detector performance. In an embodiment, the readout beam source 128 is a 635 nm laser. The hologram is read out using a 635 nm readout beam 132, which is aligned and focused to satisfy the Bragg interference condition within the hologram in the holographic medium 116. The hologram then diffracts a portion of the readout beam 132 which is detected by the readout detector 152, which in this embodiment is a CMOS camera. The readout beam 132 reads out a spatially varying index of refraction modulation induced by the X-ray. In this embodiment, the erasure beam source 160 is a 340 nm UV light source. The erasure beam 164 is a UV beam. The hologram in the holographic medium 116 can be erased by illuminating the holographic medium, which in this embodiment is a photorefractive medium, such as a photorefractive crystal, with uniform intensity UV light. In this embodiment, the imaging system makes the combination of the imaging system 148 and readout detector 152 act as a variable phase contrast optical microscope. Variable phase contrast optical microscopes are known in the art and are described in more detail in Goodman, Joseph W. Introduction to Fourier optics. Roberts and Company Publishers, 2005. Pages 312-314, which is incorporated by references for all purposes.

In this embodiment, the holographic medium 116 is undoped y-cut 500 μm thick lithium niobate. Lithium niobate is a useful material for this application because it is both photorefractive and ferroelectric. The photorefractive property uses the electro-optic effect to form a change in the index of refraction of the crystal when illuminated at photon energies above the bandgap of lithium niobate. This allows X-rays, in the 40 keV range compared with the 3.8 eV bandgap of lithium niobate, to result in a spatially varying shift in the index of refraction. This results in a spatially varying index of refraction modulation induced by the X-ray in the holographic medium 116.

Figure 4A:
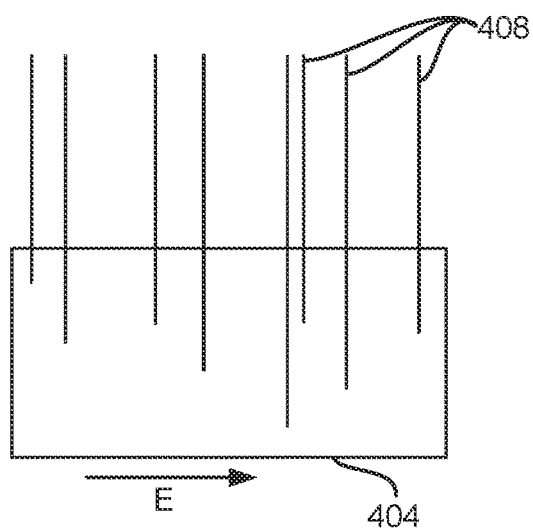
FIGS. 4A-E schematically illustrate how a hologram is formed in a crystal material by X-rays.
Figure 4B:
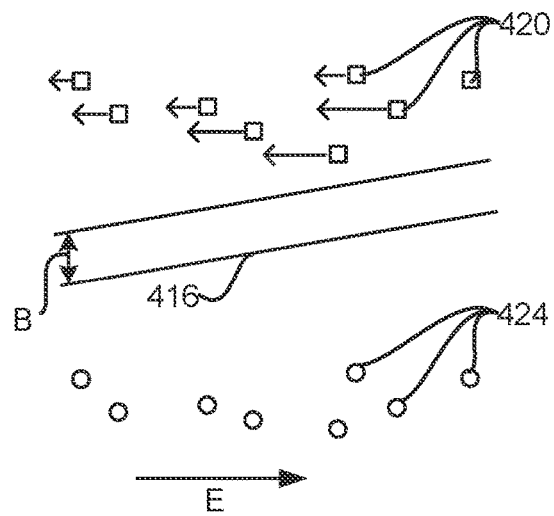
Figure 4C:
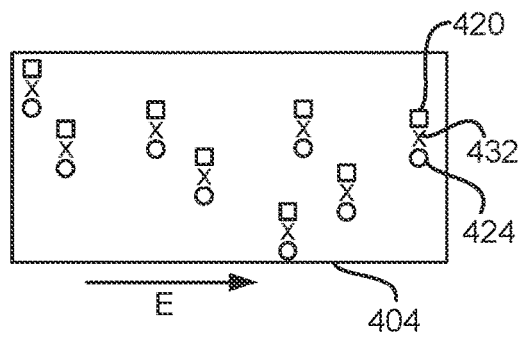

The hologram itself is written by spatially patterned X-rays which interact with the crystal material in the manner depicted in FIGS. 4A-E, creating an X-ray intensity pattern. First, detected X-rays 408 interact with the semiconductive, photorefractive crystal 404 by generating a high energy electron-hole pair that can down-scatter to form charge clouds as shown in FIG. 4A-C. FIG. 4A schematically illustrates X-rays 408 interacting with the semiconductive, photorefractive crystal 404. X-rays have greater energy than the bandgap B of the photorefractive medium, 3.8 eV in the case of lithium niobate. FIG. 4B shows how the X-rays interact with the semiconductive, photorefractive crystal, exciting electrons 420 across the photorefractive medium's bandgap 416, leaving behind high energy holes 424. An electric field E exists within the semiconductor, photorefractive crystal 404. The electric field can be either intrinsic due to a ferroelectric material or externally applied. A bandgap 416 energy of 3.8 eV is the minimum energy B needed to excite an electron 420 into a conductive band. All X-rays, by the definition of X-ray as a photon with a wavelength of less than 10 nm, have an energy greater than 124 eV. Thus all incident X-rays, upon interaction with the photorefractive crystal, are capable of imparting sufficient energy to excite an electron across the bandgap 416 of the photorefractive crystal 404. The excited electrons 420 create corresponding holes 424.

Figure 4D:
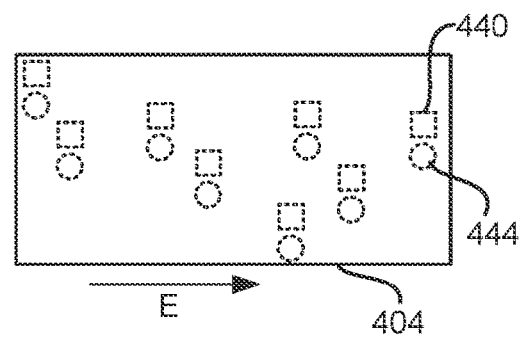
Figure 4E:
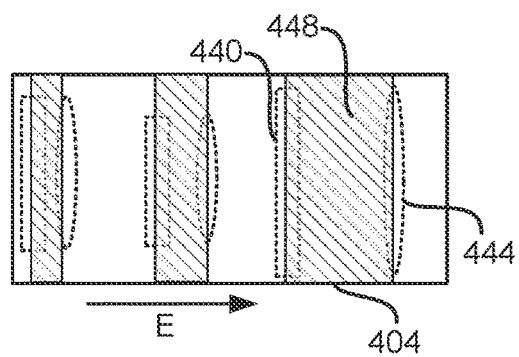

FIG. 4C is a schematic illustration of how X-ray interactions 432 form electron-hole pairs of electrons 420 and corresponding holes 424. The charge clouds dissociate in the bias field due to drift. FIG. 4D schematically illustrates how high energy charge pairs scatter to form electron charge clouds 440 and hole charge clouds 444. FIG. 4E shows how the electron charge clouds 440 and the hole charge clouds 444 further dissociate and form a space charge field 448 causing localized changes to the electric field and the index of refraction. The charges become trapped in local crystal defects to form a space charge field 448 with an associated spatially varying electric field FIG. 4E. This spatially varying electric field results in a varying shift in the permittivity along the c-axis of the photorefractive crystal. The hologram forms in real time but is also recorded semi-statically. Experimentally, the resulting hologram showed no observable change in its diffraction efficiency even months after exposure when it was not erased.

In this embodiment, the hologram is written with X-rays that have a mean energy of 40 keV using a microfocus X-ray source with an 80 kV accelerating potential. The broad spectrum produced by an X-ray tube means the hologram that is written is effectively a white light hologram with a central wavelength of 0.03 nm. In this embodiment, the hologram is read out using visible light, in order to make use of commonly available optics and photodetectors. Thus a hologram written at 0.03 nm is read using a beam with a wavelength over 4 orders of magnitude longer, at 635 nm. Reading out this hologram is possible by satisfying the Bragg condition for the thick hologram which requires precise alignment of the read out beam with the X-ray fringes. For a set fringe pitch of the X-ray hologram, $\Lambda$, the Bragg condition of the thick hologram is satisfied when $\Lambda=\lambda/2 \sin \theta$, where $\lambda$ is the wavelength of the readout beam and $\theta$ is the relative angle between the X-ray beam and optical readout beam. The hologram is read out using 635 nm light which, according to the previously mentioned equation, should be diffracted at an angle of 0.066 radians. The amount of light that is diffracted is described by the diffraction efficiency.

For a thick hologram, the diffraction efficiency, $\eta$ goes as $\eta=\sin^2(\pi d \Delta n/\lambda \cos \theta)$. $\alpha$ is the absorption coefficient of the crystal, d is the thickness of the hologram, $\lambda$ is the wavelength of the readout beam, and $\theta$ is the angle at which the Bragg condition is satisfied. The absorption of the diffracted beam is negligible for undoped lithium niobate at 635 nm. For small diffraction efficiencies, the diffraction efficiency can be approximated using the small angle approximation as $\eta=(\pi d \Delta n/\lambda \cos \theta)^2$. The definition of the electro-optic effect relative to the change in the index of refraction is $$\Delta(1/n^2)_{ij} = \Sigma r_{ijk} E_k \quad (1)$$

where i, j, and k refer to x, y, and Z. $E_k$ is the electric field along that axis and $r_{ijk}$ refers to the electro-optic coefficient tensor. Combining the electro-optic induced change to the index of refraction with the diffraction efficiency of a thick hologram yields $\Delta(E)$ is linearly proportional to the incoming X-ray fringe intensity $\phi_{X\text{-}ray}$. $\Delta(E) = A\phi_{X\text{-}ray}$ where A is a constant representing material properties such as the scattering efficiency of the X-ray, mean free path of charge carriers, and predominant carrier type.

$$\eta \approx \left(\frac{\pi a}{\lambda \cos \theta}\right)^2 \frac{n_0^6}{2} r_{33} E_{bias} A \phi_{X\text{-}ray} \quad (2)$$

Thus, the linear change in the space-charge field results in a linear change to the diffraction efficiency. This linear dependence would break down at saturation or when the small angle approximation no longer holds true, which occurs at a diffraction efficiency of approximately 30%. Because the diffraction efficiency is relatively low, at around $10^{-6}$, the detector response is linear as a function of detected X-ray dose.

In this embodiment, the hologram stored in the photorefractive crystal can be erased by illuminating the crystal with uniform UV radiation. The UV light has high enough energy to generate freed charges within the crystal. Effectively erasure is the same as writing a new, completely uniform hologram using UV light. This removes non-uniformities in the space charge field and clears the way for recording new X-ray holograms.

In an embodiment, directly imaging the hologram requires a variable phase contrast optical microscope. In this embodiment, the microscope is integrated with the rest of the holographic X-ray detector module.

The pattern recorded in the holographic medium 116 can be read out using a phase contrast optical microscope. The phase contrast optical microscope transforms information which is encoded in the phase modulation of the readout beam 132 into an amplitude modulation which can be digitized using a CCD, CMOS, or photodiode array device. The shaped readout beam 132, after passing through the holographic medium 116 is collected using a microscope objective assembly. The microscope objective is designed such that the readout beam 132 is focused at the stop plane of the microscope objective. Also at the stop plane is a phase and amplitude modulator. The phase and amplitude modulator consists of a localized area of optical attenuation and all other areas coated to impart a $\pi/2$ or $3\pi/2$ phase shift relative to the attenuated area. In some instantiations, the phase modulation is accomplished using a liquid crystal phase modulator. In some instantiations, the optical attenuation is accomplished using a liquid crystal amplitude modulator. The attenuated area is placed such that the readout beam 132, when not modified by the hologram, will be focused on that area. Modification by the hologram is meant to include all diffraction, refraction, and reflection which are caused by the hologram. All holographically modified portions of the beam pass through the phase modulated portion of the phase and amplitude modulator. The resulting light can additionally pass through a tube lens to assist with focusing before the light is detected by the readout detector 152. The holographically modified and subsequently, phase shifted light and the holographically unmodified light which has been attenuated, interfere on the readout detector 152 to form an amplitude modulated image of the recorded X-ray hologram. Linear changes in the phase modulation by the X-ray hologram can thus result in linear changes in detected image amplitude at the readout beam detector.

Figure 5:
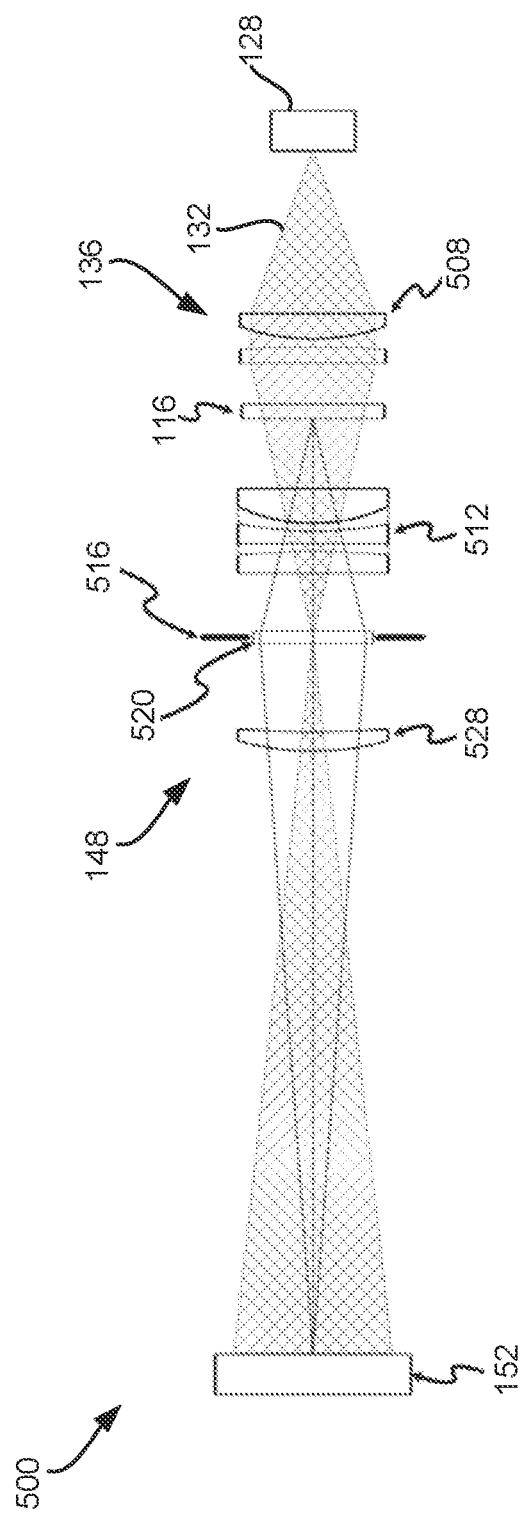
FIG. 5 is a schematic view of a phase contrast optical microscope that is used in an embodiment.

To facilitate understanding, FIG. 5 is a schematic view of a phase contrast optical microscope 500 that provides more detail to the readout forming optics 136 and imaging system 148 between readout beam source 128 and the readout detector 152, used in an embodiment. In this embodiment, the readout forming optics 136 comprises a readout forming beam forming lens 508, along the readout beam 132. The readout beam 132 passes through the holographic medium 116 to the imaging system 148. The readout beam 132 passes to a microscope objective assembly 512 of the imaging system 148. The microscope objective assembly 512 focuses the readout beam 132 at a stop plane 516. A phase and amplitude modulator 520 is placed at the stop plane 516. The readout beam 132 passes from the stop plane 516 through a tube lens 528 to the readout detector 152.

The time required for capturing an X-ray image is often limited by the desired signal to noise of the image. A high power X-ray source, capable of providing a higher flux often results in a shorter integration time.

The overall speed of this X-ray detector could be very fast. It has been shown that the X-ray generated charge scattering time is on the order of less than 100 fs and hologram formation in lithium niobate can occur in less than 2 ns when written using a high power source. Thus, with a sufficiently high flux X-ray source, the X-ray detector could form a hologram for readout in as little as 2 ns. Readout itself is only limited by the speed of the readout detector 152 as undoped lithium niobate is transparent at 635 nm, so the readout beam has no obvious power limitation. The fastest readout detector 152 available currently is capable of 1 million FPS, which is still far slower than the hologram formation time. Hologram erasure follows the same path as hologram formation and thus should take an equivalent amount of time. Thus, the factor limiting holographic X-ray detection speed is the readout detector 152 speed.

An interesting feature of this X-ray detection technique is its relatively low resource requirement. Advances in resolution and efficiency are the product of the overall technique and actually relaxes the requirements on the optics, photodetector, and X-ray interaction material relative to indirect X-ray detection. For instance, the readout detector 152, whether that is a CMOS camera, CCD camera, or photodiode array, does not need to have a particularly high quantum efficiency as any decrease in quantum efficiency can be easily compensated for by increasing the power of the readout beam. Undoped lithium niobate is already produced at industrial scales with optical quality, polished wafers that could capture a large field of view. Thus this technique could easily scale to capturing gigapixel X-ray images.

Holographic X-ray detection enables differential phase contrast X-ray imaging by achieving both the high resolution and the high quantum efficiency necessary for clinical viability. The X-ray detector in an embodiment achieves a quantum efficiency of 80% at 40 keV while also being able to resolve 208 lp/mm features. For comparison, our calculations indicate that an indirect X-ray detector using LuAG:Ce, capable of resolving 208 lp/mm, would have a quantum efficiency of roughly 2% at 40 keV. Furthermore, the ability to directly image the X-ray fringes which are necessary for X-ray DPC imaging, means that a G2 absorption grating is no longer required which decreases alignment requirement, improves quantum efficiency, and decreases imaging artifacts while providing a G2 free system. The experimental findings previously shown demonstrate that this X-ray detection technique opens several exciting avenues of research using high energy, high resolution, and high efficiency, phase sensitive X-ray imaging.

In various embodiments, the holographic (DPC) X-ray detector may be used in systems that use DPC X-ray detection such as a computed tomography system, a mammography system, a chest X-ray system, a dual energy X-ray absorptiometry (DEXA) system, an industrial nondestructive testing system, a food industry analysis system, or a security scanning system. The invention may be used in various high resolution imaging X-ray systems. In various embodiments, the readout detector 152 may be at least one of a CMOS camera, a CCD camera, a photodiode array, or a similar detector. In various embodiments, the holographic medium 116 may be at least one a photoreactive crystal and a photopolymer or similar rewritable photorecordable medium. In various embodiments, the photorefractive crystal may be at least one of a lithium niobate crystal, a barium titanate crystal, a bismuth silicon oxide crystal, a germanium silicon oxide crystal, or a strontium barium niobate crystal. In various embodiments, the readout beam source 128 is an optical light source, where optical light includes infrared, visible, and ultraviolet light. In various embodiments, the erasure beam source may be at least one of a UV light source or an X-ray source, or any beam that has a higher energy than the band gap of the recording medium. In some embodiments, the readout beam source 128 and the readout detector 152 may be separated from the rest of the system or the erasure beam source 160 may be separate from the rest of the system.

While this invention has been described in terms of several preferred embodiments, there are alterations, permutations, modifications, and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. An apparatus, comprising:
   an X-ray source for providing an X-ray along an X-ray beam path;
   a holographic medium along the X-ray beam path;
   an X-ray phase grating between the X-ray source and the holographic medium along the X-ray beam path;
   a readout beam source for providing a readout beam along a readout beam path; and a readout detector along the readout beam path, wherein the holographic medium is along the readout beam path.

2. The apparatus, as recited in claim 1, further comprising an erasure beam source providing an erasure beam along an erasure beam path, wherein the holographic medium is along the erasure beam path.

3. The apparatus, as recited in claim 2, wherein the erasure beam source is a UV light source.

4. The apparatus, as recited in claim 1, further comprising an object support for supporting an object along the X-ray beam path between the X-ray phase grating and the holographic medium.

5. The apparatus, as recited in claim 1, wherein the readout beam source is an optical light source and wherein the readout detector is a camera or photodiode array.

6. The apparatus, as recited in claim 1, wherein the holographic medium is a photorefractive medium.

7. The apparatus, as recited in claim 1, further comprising a controller electrically connected to the X-ray source, the readout beam source, and the readout detector, wherein the controller comprises computer readable media, comprising:

computer readable code for causing the X-ray source to generate an X-ray beam to pass through the X-ray phase grating and an object to the holographic medium, wherein the X-ray beam creates an X-ray DPC holographic image of the object in the holographic medium;

computer readable code causing the readout beam source to direct the readout beam through the holographic medium to the readout detector; and computer readable code for receiving readout data from the readout detector and generating and displaying an X-ray DPC image of the object from the readout data.

8. A method, for detecting a spatially varying X-ray intensity pattern, comprising:

passing the X-rays through a phase grating and an object;

directing X-rays into photorefractive medium; and reading out a spatially varying index of refraction modulation induced by the X-ray intensity pattern in the photorefractive medium.

9. The method, as recited in claim 8, further comprising applying an erasure beam to the photorefractive medium after reading out the spatially varying index of refraction modulation induced by the X-ray intensity pattern in the photorefractive medium.

10. The method as recited in claim 9, wherein the erasure beam is a UV beam.

11. The method, as recited in claim 8, wherein the reading out the spatially varying index of refraction modulation induced by the X-ray intensity pattern in the photorefractive medium, comprises:

passing a readout beam through the photorefractive medium; and measuring the readout beam after passing through the photorefractive medium.

* * * * *